(12) United States Patent  
Beens et al.

(10) Patent No.: US 7,979,139 B2
(45) Date of Patent: Jul. 12, 2011

(54) RADIO FREQUENCY DIATHERMY APPLICATION SYSTEM AND DEVICE

(75) Inventors: Jason A. Beens, San Antonio, TX (US); Scott R. Hinson, Austin, TX (US); Daniel E. Nesthus, San Antonio, TX (US)

(73) Assignee: ReGear Life Sciences, Inc., Pittsburgh, PA (US)

(*) Notice: Subject to any disclaimer, the term of this patent is extended or adjusted under 35 U.S.C. 154(b) by 230 days.

(21) Appl. No.: 11/177,239

(22) Filed: Jul. 8, 2005

(65) Prior Publication Data

US 2006/0119462 A1 Jun. 8, 2006

Related U.S. Application Data

(63) Continuation-in-part of application No. 11/002,957, filed on Dec. 2, 2004, now abandoned.

(51) Int. Cl.
*A61F 7/00* (2006.01)
(52) U.S. Cl. ............ 607/101; 607/98; 607/99; 607/100; 607/102; 607/103
(58) Field of Classification Search ............ 606/98–103; 607/98–103
See application file for complete search history.

(56) References Cited

U.S. PATENT DOCUMENTS

| | | | | | |
|---|---|---|---|---|---|
| 1,853,814 A | * | 4/1932 | Huth | ............................. | 607/152 |
| 2,130,758 A | * | 9/1938 | Rose | ............................. | 607/155 |
| 2,223,447 A | * | 12/1940 | Hathaway | ........................ | 607/98 |
| 3,952,751 A | * | 4/1976 | Yarger | ............................. | 607/71 |
| 3,978,864 A | * | 9/1976 | Smith | ............................. | 607/155 |
| 4,117,846 A | * | 10/1978 | Williams | ........................ | 606/32 |
| 4,140,130 A | * | 2/1979 | Storm, III | ........................ | 607/154 |
| 4,186,294 A | * | 1/1980 | Bender | .......................... | 219/527 |
| 4,636,730 A | * | 1/1987 | Bottomley | ........................ | 324/322 |
| 4,974,587 A | * | 12/1990 | Turner et al. | .................. | 607/101 |
| 5,186,181 A | * | 2/1993 | Franconi et al. | .............. | 607/156 |
| 5,584,863 A | * | 12/1996 | Rauch et al. | ...................... | 607/2 |
| 6,060,882 A | * | 5/2000 | Doty | ............................. | 324/318 |
| 6,094,599 A | * | 7/2000 | Bingham et al. | .............. | 607/149 |
| 6,353,763 B1 | * | 3/2002 | George et al. | .................. | 607/50 |
| 2004/0230226 A1 | | 11/2004 | Bingham et al. | .................. | 607/3 |
| 2006/0052855 A1 | * | 3/2006 | Docherty et al. | ............. | 607/108 |

FOREIGN PATENT DOCUMENTS

| EP | 0 209 246 | 1/1987 |
|---|---|---|
| GB | 283 236 | 1/1928 |

OTHER PUBLICATIONS

Lehmann "Therapeutic heat and cold," Fourth Edition, pp. 196-200 and 458-477, 1990.
Michlovitz "Thermal agents in Rehabilitation" Third Edition, pp. 220, 225, 1996.

* cited by examiner

*Primary Examiner* — Roy D Gibson
*Assistant Examiner* — Kaitlyn E Helling
(74) *Attorney, Agent, or Firm* — The Webb Law Firm (57) ABSTRACT

A radio frequency diathermy application device, including a flexible pad and a flexible coil structure coupled to and supported by the pad The flexible coil structure has a flexible spiral-like primary winding and a flexible spiral-like secondary winding coupled to the primary winding, the primary and secondary windings each substantially lying in separate substantially parallel planes when the pad is in an unflexed state.

31 Claims, 6 Drawing Sheets

RADIO FREQUENCY DIATHERMY APPLICATION SYSTEM AND DEVICE

This application is a continuation-in-part of application Ser. No. 11/002,957, entitled "Radio Frequency Diathermy Application System and Device" filed Dec. 2, 2004, now abandoned.

BACKGROUND OF THE INVENTION

1. Field of the Invention

The present invention relates to radio frequency diathermy application systems and devices.

2. Description of Related Art

Radio Frequency (RF) coil systems have been used to apply heat to various portions of a patient's body, including limbs. Such systems have provided therapeutic medical treatment, including muscle healing, wound healing, and warming of hypothermia victims.

For example, U.S. Pat. No. 4,527,550 describes a coil designed for use under full-wave operation at coil-wire length resonance. This system is limited to operation in an electromagnetic shielded room in order to meet FCC requirements. U.S. Pat. No. 5,160,828 describes an apparatus for warming the extremities of a subject so that the subject can perform certain tasks in a cold environment. This apparatus can be operated in free-space, without shielding, while complying with environmental regulations.

U.S. Pat. Nos. 6,094,599, and 6,853,865 (the disclosures of each of which are expressly incorporated herein by reference), each disclose RF diathermy apparatus for warming the extremities of a subject, including, for example, a hand, wrist, forearm, elbow, ankle, and/or knee. Such apparatus may also be operated in free-space, without shielding, while complying with environmental regulations. These devices may be used for treating slow or non-healing wounds due to vascular inefficiency, diabetic peripheral neuropathy, microangiography, microvascular disease, or compression neuropathies such as Carpal Tunnel Syndrome. However, prior apparatus for application of RF diathermy have been substantially cylindrical in shape, or have required additional materials such as towels to provide for safe operation on large substantially planar muscle groups within the body, including, for example, the back, abdomen, chest, and/or neck areas. The absence of the additional material could result in overheating of the patient's subcutaneous fat layers and ultimately discomfort and injury.

SUMMARY OF THE INVENTION

The present invention solves the above-noted discrepancies existing in prior approaches, and in one embodiment provides a radio frequency diathermy application system and device, including a flexible pad; and a flexible coil structure coupled to and supported by the pad. The flexible coil structure has a flexible spiral-like primary winding and a flexible spiral-like secondary winding coupled to the primary winding, the primary and secondary winding each substantially lying in separate substantially parallel planes when the pad is in an unflexed state.

In accordance with one aspect of the invention, the primary and secondary windings may each be substantially two-dimensional spirals when the pad is in the unflexed state, with the two-dimensional spirals being, for example, Archimedean spirals.

In accordance with another aspect of the invention, the primary and secondary windings may each have a substantially common central axis with the windings being displaced from one another along the axis. In accordance with yet another aspect of the invention, a turns ratio of the secondary winding to the primary winding may be approximately 3:1.

In accordance with another aspect of the invention, the flexible pad structure has a thickness chosen to minimize the effects of stray electrical fields (E-fields) on the subcutaneous fat cells of the patient. In accordance with another aspect of the invention, the flexible pad structure is semi-rigid to prevent gross misshaping of the device so as to prevent inadvertent tuning of the device to resonance. This also minimizes the use of the device on non-muscular tissue providing lower device temperatures and stress on the device. In accordance with another aspect of the invention, the frequency tuning capability of the device may be limited so as to only function when used on a patient.

The system of the present invention may include a radio frequency diathermy generator for driving the radio frequency diathermy application device These, and other, aspects of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The drawings accompanying and forming part of this specification are included to depict certain aspects of the invention. A clearer conception of the invention will become more readily apparent by referring to the exemplary, and therefore nonlimiting, embodiments illustrated in the drawings, wherein like reference numerals (if they occur in more than one view) designate the same or similar elements. The invention may be better understood by reference to one or more of these drawings in combination with the description presented herein. It should be noted that the features illustrated in the drawings are not necessarily drawn to scale.

DESCRIPTION OF ILLUSTRATIVE EMBODIMENTS

The invention and the various features and advantageous details thereof are explained more fully with reference to the non-limiting embodiments that are illustrated in the accompanying drawings and detailed in the following description. It should be understood that the detailed description and the specific examples, while indicating specific embodiments of the invention, are given by way of illustration only and not by way of limitation. Various substitutions, modifications, additions, and/or rearrangements within the spirit and/or scope of the underlying inventive concept will become apparent to those of ordinary skill in the art from this disclosure.

The RF diathermy application device, representing an embodiment of the invention, facilitates application of RF diathermy to large, substantially planar, muscle groups within the body, including the chest, abdomen, back and/or neck.

Figure 1:
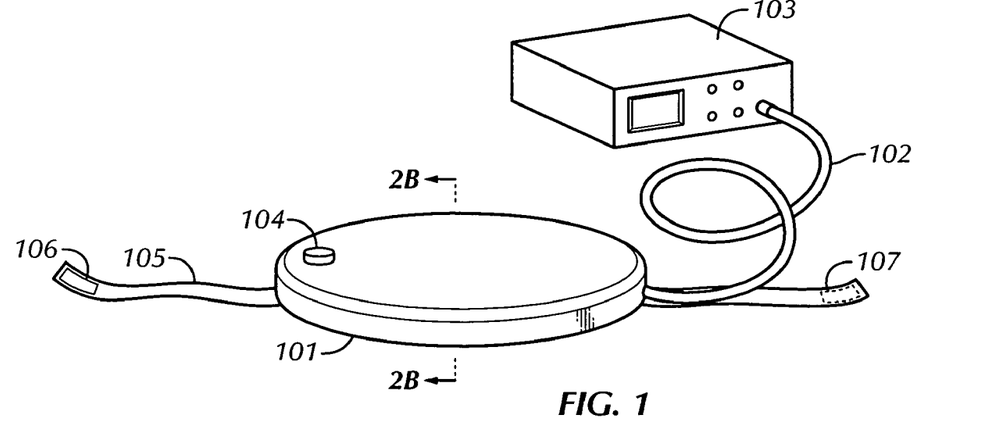
FIG. 1 is a radio frequency diathermy system and device in accordance with an embodiment of the present invention.

Referring to FIG. 1, a functional block diagram of an RF diathermy application system and device is depicted. The system includes an RF diathermy application device 101, in the form of a pad-shaped structure, which will be described in more detail below. Device 101 is connected to a RF generator 103 by a coaxial cable 102. A tuning circuit 104 is coupled to a flexible coil structure within device 101, as will be described in more detail below. Attached to device 101 is securing strap 105, including a fastening structure 106, 107 for affixing device 101 to a patient under treatment. Fastening structure 106, 107 may be, for example, a hook-and-loop type fastener, but other types of fasteners would also be acceptable.

RF diathermy application device 101 is a flexible structure which assumes a substantially planar form when in its unflexed state, as shown in FIG. 1. Device 101 is flexible so as to conform to the surface of an area to be treated, typically, large substantially planar muscle groups within the human body, including, for example, the back, abdomen, chest and/or neck areas.

RF generator 103 is described in detail with reference to FIG. 6. In one embodiment of the invention, generator 103 produces RF power at 27.12 MHz (11.06 meters), however other RF frequencies may also be acceptable, including, for example, 13.56 MHz (22.12 meters).

Figure 2A:
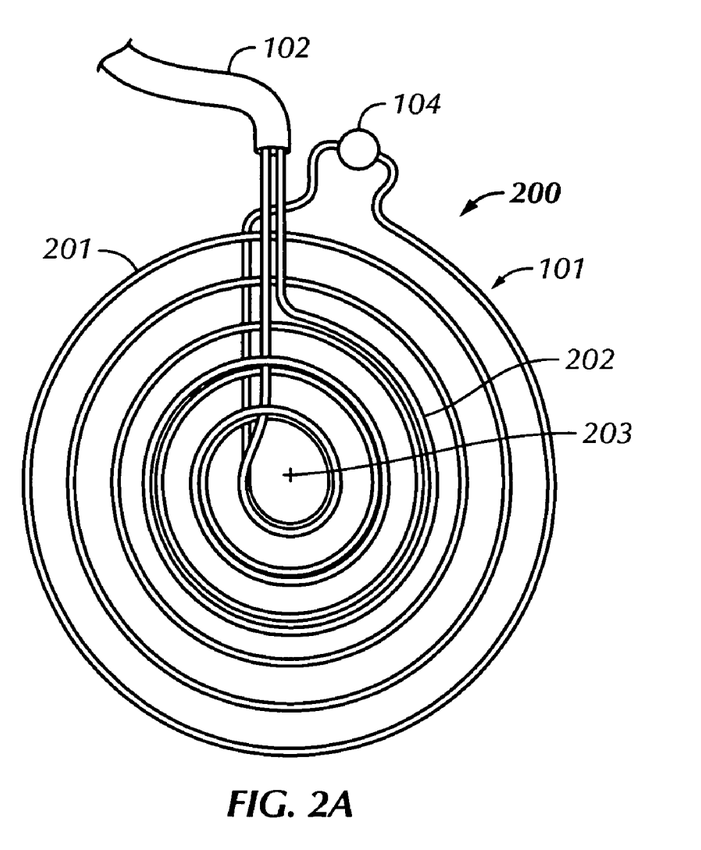
FIG. 2A is a schematic representation of a flexible coil structure usable in the device of FIG. 1.

Referring to FIG. 2A, a schematic representation of a flexible coil structure 200, usable within device 101 is presented. Flexible coil structure 200 includes a flexible spiral-like primary winding 202 which is coupled to a flexible spiral-like secondary winding 201. Tuning circuit 104 may include a tuning capacitor as shown. Primary winding 202 is connected to coaxial cable 102, and to RF diathermy generator 103 (see also, FIG. 1).

Flexible spiral-like windings 201 and 202 are shown in FIG. 2A as they would appear when device 101 is in an unflexed state. In that unflexed state, windings 201 and 202 take the form of substantially two-dimensional spirals, each occupying a separate plane, with the separate planes being substantially parallel to each other. In addition, windings 201 and 202 may have a substantially common central axis 203 and may be displaced from one another along the central axis 203. In one embodiment, windings 201 and 202 are flexible so they may flex with device 101. In a specific embodiment, windings 201 and 202 are 18 gauge. stranded silver-plated copper wire insulated with polytetrafluoroethylene (PTFE). Other types of wires and insulations would also be acceptable.

Tuning circuit 104 may be a variable capacitor as shown. However, other forms of tuning circuits may also be acceptable, including tuning circuits including inductive components or tuning circuits including both inductive and capacitive components. A matching circuit may also be included to match the unbalance coaxial cable 102 with the balanced coil structure 200. The matching circuit may include a balun. The tuning range of the tuning circuit 104 may be selected so as to prevent resonance when muscle tissue is not coupled to the device. This is compatible with sensing circuitry in the RF generator 103 to prevent operator error. Additionally, limiting the tuning range provides easier operation in a manually controlled system. The appropriate tuning range depends on the specific embodiment, but is well understood in the art of RF diathermy. In one embodiment, tuning circuit 104 may be a high voltage PTFE trimmer capacitor with a tuning range of between 5 and 20 picoFarads. One acceptable trimmer capacitor includes a type NT25-6 trimmer capacitor available from Voltronics of Denville, N.J. Other types of variable capacitors and other types of tuning circuits would also be acceptable.

Figure 2B:
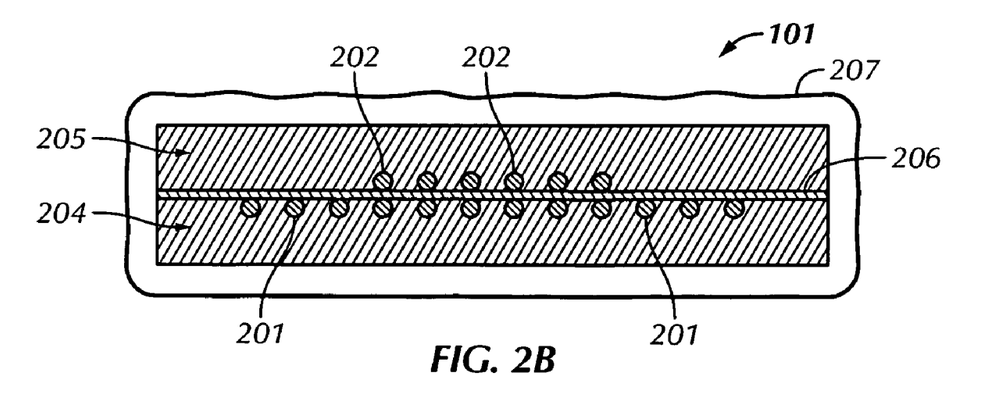
FIG. 2B is cross-sectional view taken through section 2B-2B of FIG. 1.

Referring now to FIG. 2B, represented is a cross-section through section 2B-2B of RF application device 101 of FIG. 1 showing the mechanical configuration of windings 201 and 202. Referring to FIG. 2B, secondary winding 201 is embedded within flexible pad 204 and primary winding 202 is embedded within flexible pad 205. Primary winding 202 and secondary winding 201 are separated from each other by an insulating spacer 206. Pads 204 and 205 and spacer 206, incorporating windings 201 and 202 are bonded together to form a substantially unified structure, using an appropriate bonding method, such as, for example, adhesive or ultrasonic bonding. The unified structure provides stiffness that retards gross misshaping of the device and prevents inadvertent tuning to resonance other than through the tuning circuit 104. This feature also discourages application of the device to non-muscular tissue. Flexible pad 204 also provides space between the patient and the secondary winding 201 to reduce the effects of stray E-fields on subcutaneous fat in the patient as well as the immediate environment. The flexible coil structure including flexible primary winding 202 and flexible secondary winding 201 embedded within pads 204 and 205, is enclosed by outer sheath 207.

In one specific embodiment, pads 204 and 205 may be made from closed-cell polyethylene foams with thermo resistance, for example, type M200 Minicell brand material available from Voltek LLC, although other types of flexible material would also be acceptable. In addition, insulating spacer 206, which serves to physically separate and electrically insulate primary winding 201 and 202, may be made from any flexible insulating material with thermo resistance, for example, polyethylene. In one illustrative embodiment, barrier 206 is a flexible polyethylene sheet with a thickness of 160 millimeters, and flexible pads 204 and 205 may have a thickness of approximately 1.25 centimeters, however, other thicknesses and materials would also be acceptable.

Figure 3:
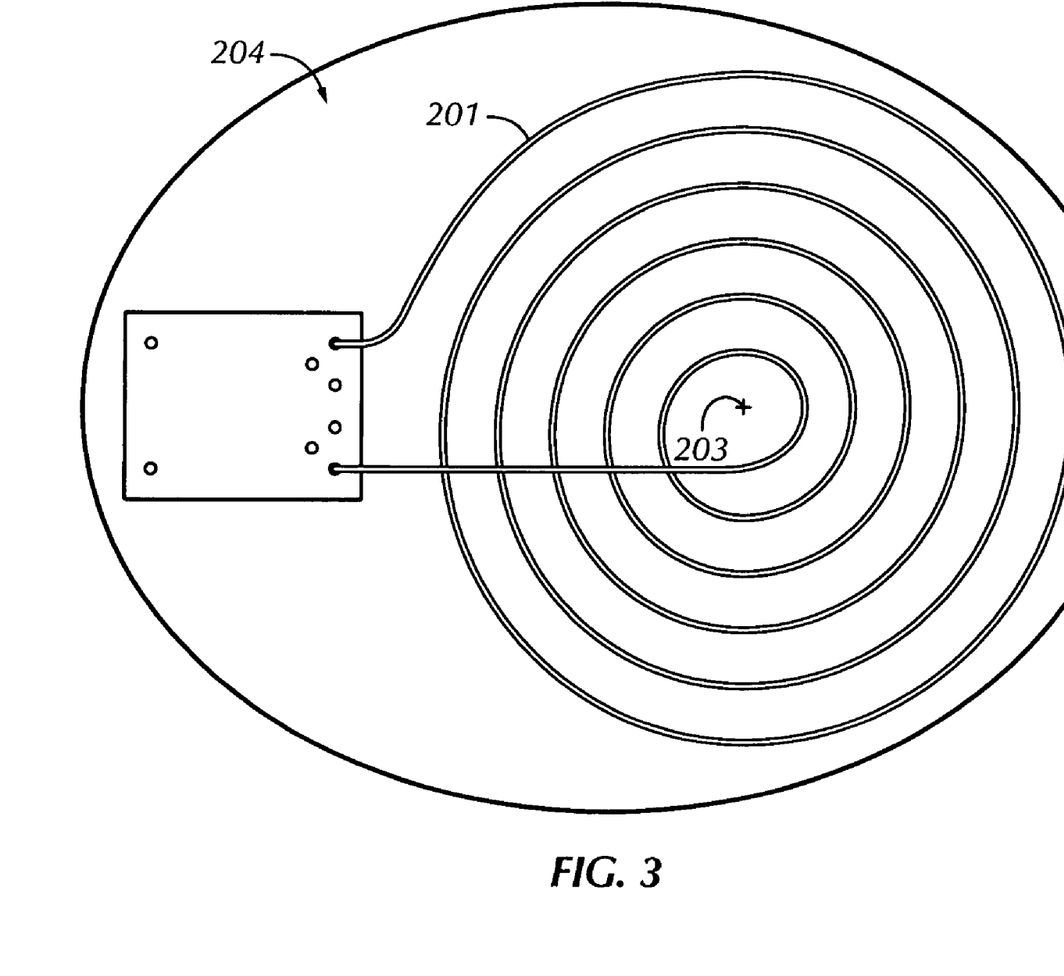
FIGS. 3 and 4 are plan views of coils useable in the device of FIG. 1.
Figure 4:
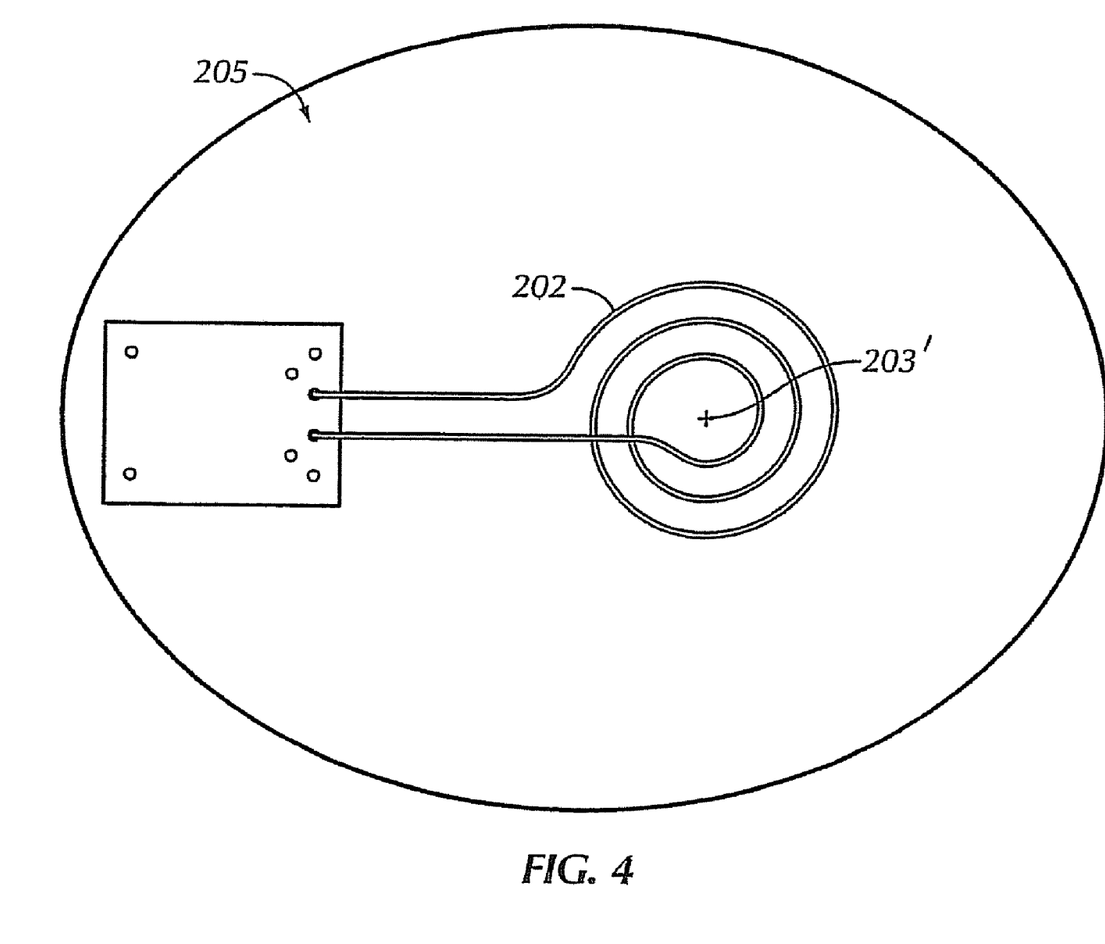

Referring now to FIGS. 3 and 4, FIG. 3 is a plan view of secondary winding 201 embedded within slotted pad 204, and FIG. 4 is a plan view of primary winding 202 embedded within slotted pad 205. Each one of primary winding 202 and secondary winding 201 may assume a spiral-like shape such as the Archimedean spiral depicted in FIGS. 3 and 4. However, other spiral-like forms would also be acceptable, including, for example, square spirals, triangular spirals, logarithmic spirals, hyperbolic spirals, or parabolic spirals. Other forms of spirals would also be acceptable.

Regardless of the particular type of spiral, each of spiral-like windings 201 and 202 are substantially two-dimensional, and substantially lie in different spaced-apart parallel planes when RF diathermy application device 101 is unflexed.

As may be seen with reference to FIGS. 3 and 4, each of windings 201 and 202, are formed about respective central axes 203 and 203'. In some embodiments, axes 203 and 203' may be the same, however, in other embodiments, there may be an offset between axes 203 and 203'. In addition, the turns ratio of secondary 201 to primary 202 in the disclosed embodiment is 3:1 however, other turns ratios may also be acceptable.

Figure 5:
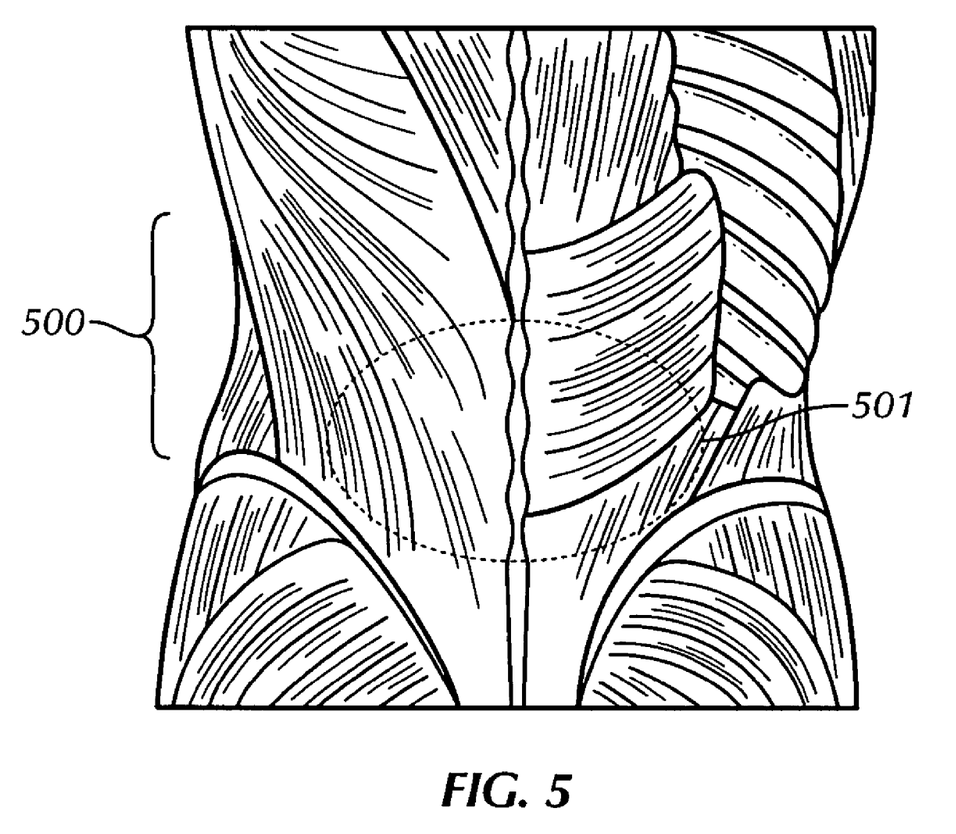
FIG. 5 is a representation of human musculature illustration a potential application of the present invention.

Referring now to FIG. 5, depicted is a representation of the musculature of the human lumbar region 500. Area 501 is depicted as an example of a large substantially planar muscle group within the human body, to which RF diathermy application device 101 may be applied. Of course, other substantially planar muscle groups elsewhere in the body, for example, other parts of the back, abdomen, chest and/or neck areas would also benefit from use of the present invention.

Figure 6:
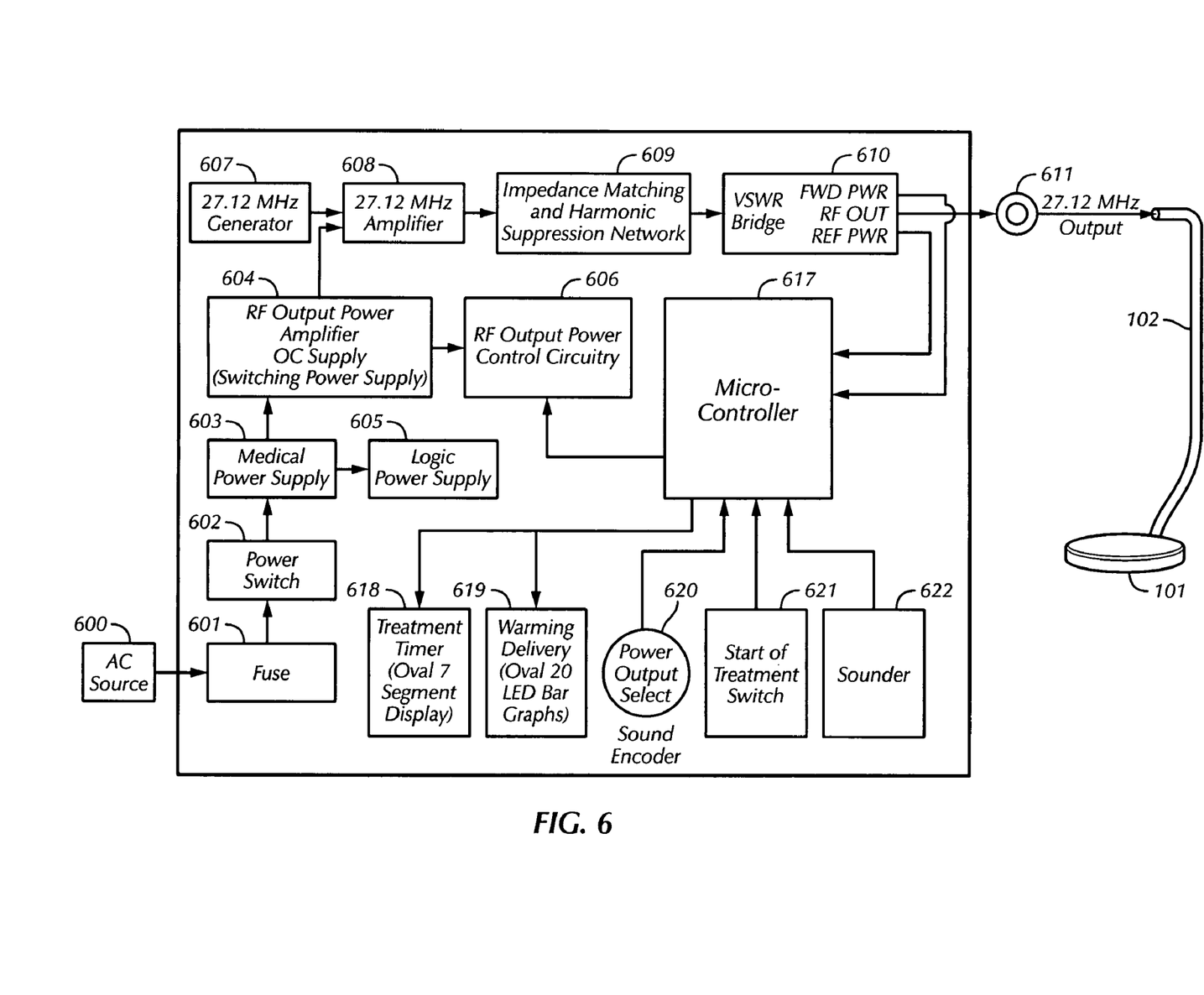
FIG. 6 is a block diagram of a short-wave diathermy generator (SWDG), representing an embodiment of the invention.

Referring to FIG. 6, a block diagram of a short-wave diathermy generator 103 is depicted that may be used in the embodiment of FIG. 1. It will be understood however that other RF generators may also be used without departing from the scope of the invention. An AC source 600 is coupled to a power switch 602 via a fuse 601. The power switch 602 is coupled to a medical power supply 603. The medical power supply 603 is coupled to an RF output power amplifier DC supply 604 and to a logic power supply 605. The RF output power amplifier 604 may include a switching power supply that is coupled to a 27.12 MHz amplifier 608 and to a microcontroller 617 via an RF power output control circuitry 606.

A 27.12 MHz generator 607 is coupled to a first impedance matching and harmonic suppression network 609 via the 27.12 MHz amplifier 608. The first impedance matching and harmonic suppression network 608 is coupled to a 27.12 MHz output 611 via a VSWR bridge 610. An RF diathermy garment lead 102 is coupled to the 27.12 MHz output connector 611, and connects the short wave diathermy generator 103 to RF diathermy application device 101. The VSWR bridge 610 is coupled to the microcontroller 617 via a forward power line and a reflected power line. The microcontroller 617 is coupled to a treatment timer 618, a warming delivery indicator 619, a power output selector 620, a start of treatment switch 621, and a sounder 622.

The short-wave diathermy generator is powered from an AC source 600, and is capable of producing RF power at 27.12 MHz (11.06 meters). Other frequencies would also be acceptable, including, for example, 13.56 MHz (22.12 meters). In one embodiment, the short wave diathermy generator provides an indication of the RF power available and the RF power delivered. The generator may utilize the VSWR bridge 610 to measure the effects of the RF load on itself and automatically reduce power when the system is not coupled to a patient by detecting a change in impedance. The VSWR bridge 610 may also be used to control the front panel display and RF protection circuitry built into the generator.

The invention may include a device for RF diathermy treatment. The invention may also include an RF diathermy coil assembly.

The terms a or an, as used herein, are defined as one or more than one. The terms including and/or having, as used herein, are defined as comprising (i.e., open language). The term coupled, as used herein, is defined as connected, although not necessarily directly, and not necessarily mechanically.

All of the disclosed embodiments of the invention may be made and used without undue experimentation in light of the disclosure. The invention is not limited by theoretical statements recited herein. Although the best mode of carrying out the invention contemplated by the inventors is disclosed, practice of the invention is not limited thereto.

In addition, while the RF diathermy coil assembly described herein may be a separate module, it will be manifest that the RF diathermy coil assembly may be integrated into the system with which it is associated.

The appended claims are not to be interpreted as including means-plus-function limitations. Specific embodiments of the invention are differentiated by the appended dependent claims and their equivalents.

The invention claimed is:

1. A radio frequency diathermy application device for treating a patient, comprising:
    a generator for generating radio frequency (rf) power; and
    a diathermy device, comprising:
        a flexible pad; and
        a flexible coil structure coupled to and supported by the flexible pad, including:
            a flexible spiral-like primary winding; and
            a flexible spiral-like secondary winding coupled to the primary winding, the primary and secondary windings each substantially lying in separate substantially parallel planes when the flexible pad is in an unflexed state, wherein:
    the flexible pad includes first and second flexible pads, the flexible spiral-like primary winding embedded within the first flexible pad, and the flexible spiral-like secondary winding embedded within the second flexible pad; and
    the flexible coil structure includes an insulating spacer disposed between the first and second flexible pads separating the flexible spiral-like primary winding and the flexible spiral-like secondary winding, wherein the insulating spacer and the first and second flexible pads are formed of different materials.

2. The radio frequency diathermy application device of claim 1, the primary and secondary windings each comprising substantially two-dimensional spirals when the flexible pad is in an unflexed state.

3. The radio frequency diathermy application device of claim 2, the primary and secondary windings each comprising an Archimedean spiral.

4. The radio frequency diathermy application device of claim 2, the primary and secondary windings each having a substantially common central axis, and being displaced from one another along the axis.

5. The radio frequency diathermy application device of claim 1, a turns ratio of the secondary winding to the primary winding being approximately 3:1.

6. The radio frequency diathermy application device of claim 1, at least one of the primary or secondary windings comprising a woven wire conductive coil.

7. The radio frequency diathermy application device of claim 6, the conductive coils adapted to flex with the pad.

8. The radio frequency diathermy application device of claim 1, further comprising a tuning circuit coupled to the secondary winding.

9. The radio frequency diathermy application device of claim 8, the tuning circuit comprising a variable capacitor.

10. The radio frequency diathermy application device of claim 8, the tuning circuit having a limited tuning range such that the device is incapable of resonating in the absence of a load.

11. The radio frequency diathermy application device of claim 1, further comprising a radio frequency power source coupled to the primary winding.

12. The radio frequency diathermy application device of claim 11, wherein the radio frequency power source produces power at a frequency of approximately 27.12 MHz.

13. The radio frequency diathermy application device of claim 11, wherein the radio frequency power source produces power at a frequency of approximately 13.56 MHz.

14. The radio frequency diathermy application device of claim 1, wherein the first or second flexible pad has a thickness of about 1.25 centimeters.

15. A radio frequency diathermy application system, comprising:

a radio frequency power source coupled to a flexible spiral-like primary winding; and a radio frequency application device including a flexible pad incorporating a flexible coil structure therewith, the flexible coil structure having the flexible spiral-like primary winding and a flexible spiral-like secondary winding coupled to the flexible spiral-like primary winding, wherein:

the flexible pad includes first and second flexible pads, the primary winding embedded in the first flexible pad, the secondary winding embedded in the second flexible pad; and an insulating spacer is disposed between the first and second flexible pads separating the primary and secondary windings, the insulating spacer being formed of a different material than the first and second flexible pads.

16. The radio frequency diathermy application system of claim 15, further comprising, a tuning circuit coupled to the secondary winding.

17. The radio frequency diathermy application system of claim 16, the tuning circuit comprising a variable capacitor.

18. The radio frequency diathermy application system of claim 16, the tuning circuit having a limited tuning range such that the device is incapable of resonating in the absence of a load.

19. The radio frequency diathermy application system of claim 15, the primary and secondary windings each comprising substantially two-dimensional spirals when the flexible pad is in an unflexed state.

20. The radio frequency diathermy application system of claim 19, the primary and secondary windings each comprising an Archimedean spiral.

21. The radio frequency diathermy application system of claim 15, a turns ratio of the secondary winding to the primary winding being approximately 3:1.

22. The radio frequency diathermy application system of claim 15, at least one of the primary or secondary windings comprising a woven wire conductive coil.

23. The radio frequency diathermy application system of claim 22, the conductive coils flexing with flexing of the pad.

24. The radio frequency diathermy application system of claim 15, the radio frequency power source producing power at a frequency of approximately 27.12 MHz.

25. The radio frequency diathermy application system of claim 15, the radio frequency power source producing power at a frequency of approximately 13.56 MHz.

26. The radio frequency diathermy application device of claim 15, wherein the first or second flexible pad has a thickness of about 1.25 centimeters.

27. The radio frequency diathermy device of claim 26, wherein each of the primary winding and secondary winding are insulated.

28. The radio frequency diathermy device of claim 27, wherein each of the primary winding and the secondary winding are insulated wire.

29. A radio frequency diathermy application device, comprising:

a flexible pad structure, including first and second flexible pads; and a flexible coil structure coupled to and supported by the flexible pad, including:

a flexible spiral-like primary winding embedded within the first flexible pad;

a flexible spiral-like secondary winding coupled to the primary winding and embedded within the second flexible pad, the primary and secondary windings each substantially lying in separate substantially parallel planes when the flexible pad structure is in an unflexed state; and an insulating spacer disposed between the first and second flexible pads separating the primary winding and the secondary winding, wherein the insulating spacer and the first and second flexible pads are formed of different materials.

30. The radio frequency diathermy application device of claim 29, wherein the flexible pad is made of a foam and the insulator is made of a non-foam material.

31. The radio frequency diathermy application device of claim 29, wherein the insulator is polyethylene sheet.

* * * * *

UNITED STATES PATENT AND TRADEMARK OFFICE
CERTIFICATE OF CORRECTION

| | | |
|---|---|---|
| PATENT NO. | : 7,979,139 B2 | Page 1 of 1 |
| APPLICATION NO. | : 11/177239 | |
| DATED | : July 12, 2011 | |
| INVENTOR(S) | : Jason A. Beens | |

It is certified that error appears in the above-identified patent and that said Letters Patent is hereby corrected as shown below:

Title Page, see item (57) Abstract, Line 3, "pad The" should read -- pad. The --

Column 8, Line 7, Claim 26, delete "device" and insert -- system --

Column 8, Line 10, Claim 27, delete "device" and insert -- application system --

Column 8, Line 13, Claim 28, delete "device" and insert -- application system --

Signed and Sealed this
Third Day of January, 2012

David J. Kappos
*Director of the United States Patent and Trademark Office*